United States Patent [19]
Sullivan, Jr.

[11] 3,944,427
[45] Mar. 16, 1976

[54] GELABLE AND GELLED COMPOSITIONS
[75] Inventor: John P. Sullivan, Jr., Malden, Mass.
[73] Assignee: Itek Corporation, Lexington, Mass.
[22] Filed: Aug. 11, 1972
[21] Appl. No.: 279,915

Related U.S. Application Data
[62] Division of Ser. No. 26,098, April 6, 1970, Pat. No. 3,700,451.

[52] U.S. Cl. ................................ 106/208; 252/316
[51] Int. Cl.² ............................................ C08L 5/00
[58] Field of Search ............ 106/208, 205; 252/311, 252/316

[56] References Cited
UNITED STATES PATENTS

| | | | |
|---|---|---|---|
| 3,054,689 | 9/1962 | Jeanes | 106/208 |
| 3,669,688 | 6/1972 | Thompson | 106/205 |
| 3,681,254 | 8/1972 | Becker | 106/208 |

*Primary Examiner*—Theodore Morris
*Attorney, Agent, or Firm*—Homer O. Blair; Robert L. Nathans; David E. Brook

[57] ABSTRACT

Gelable or gelled compositions are disclosed which comprise a liquid medium, agar, and a combination of natural gum gel-forming agents including xanthan gum and locust bean gum. The gelable dispersions are easily gelled by heating to the gel-critical temperature and subsequently cooling them below the setting temperature. In the gelled state, these compositions are useful as carriers for many types of liquids including photo-processing solutions and therapeutic solutions.

4 Claims, No Drawings

GELABLE AND GELLED COMPOSITIONS

This is a division of application Ser. No. 026,098, filed Apr. 6, 1970, now U.S. Pat. No. 3,700,451, issued Oct. 24, 1972.

BACKGROUND OF THE INVENTION

1. Field of the Invention

This invention relates to gelable and gelled compositions and more particularly to gelable and gelled compositions containing agar.

2. Prior Art

Many gel-like compositions have been described in the literature for a variety of applications. The gelable and gelled compositions described herein, however, are significantly different from various prior art formulations categorized as viscous, jelly-like, rubbery, pastes, creams, etc. These gelled compositions comprise true gels which have a rigidity and form common to solids. Viscosity is a meaningless term in describing these gelled solutions because the gel formers form a three-dimensional network which contains the liquid components and this three-dimensional network is broken down in attempts to measure viscosity. One method of characterizing these gelled compositions is in terms of their break strengths and elasticities.

Gelable dispersions are also described herein which comprise dispersions of gel formers in a liquid medium which is to be converted to the gelled state. Since all of these dispersions contain agar, gelation is accomplished by heating the dispersion above the gel-critical temperature and subsequently cooling the dispersion below the gelation or setting temperature.

The compositions described herein contain agar, which is a natural gel-forming agent derived from the red seaweed family. Agar gels traditionally have relatively low-setting temperatures contrasted to gels formed with other gel formers. In many gel applications, it is particularly desirable to take advantage of agar's low-setting temperature.

One example of a situation where it is advantageous to use the low-setting agar in gelled liquids is where the gelled liquid serves as a carrier for a therapeutic agent which is intended for topical application to the human body. If agar gelable compositions could be used for this purpose, application of the composition to the patient's body could be greatly simplified because of the low-setting temperature of agar gels. In other words, the gelled compositions could be formed upon the patient's body, which has heretofore been impossible due to the high setting temperatures of presently available gelable compositions.

It would also be a particular advantage to be able to use low-setting agar gels in photoprocessing applications. In photoprocessing, gelable dispersions are heated above their critical temperature and then extruded onto exposed photosensitive media whereupon they set upon cooling and are stripped off after processing. In many film processing applications, particularly color film, it is critically important that the gelable material applied to the film have as low a temperature as possible. The high-setting temperatures of formerly available gelable dispersions had a tendency to destroy good color balance due to overprocessing of the top layer in color film processing.

Despite their appeal because of their low-gelling temperature, solutions gelled solely with agar have not been used in many possible applications because they have simply not had the other properties required for these applications. For example, solutions gelled solely with agar are very inelastic and brittle and therefore not suitable for extrusion and removal from a photosensitive medium nor are they suitable for topical application of therapeutic solutions. For extrusion, the agar gels have another drawback in that at the elevated extrusion temperatures these gelable dispersions have extremely low viscosities which give them a watery consistency unsuitable for extrusion. Therefore, it has long been desirable to modify agar gels to improve these properties.

While many attempts have been made to improve these properties, none have been successful to date. The addition of thickeners and viscousing agents to improve the viscosity of the gelable dispersions at extrusion temperatures has resulted in gelled solutions with very low break strengths. Combining other gelling agents with agar has customarily resulted in the gel formers tending to compete with each other providing adverse results.

SUMMARY OF THE INVENTION

In an embodiment of the invention, gelable and gelled compositions are formed wherein a liquid medium contains agar and a combination of natural gum gel-forming agents including xanthan gum and locust bean gum. Agar is present in an amount of 0.5%–5%, and the combination of natural gum gel-forming agents is present in smaller amounts of 0.1%–0.5%. Since all of these gel formers are temperature dependent, gelation is accomplished by heating the gelable composition to a temperature above the gel critical temperature and subsequently cooling the compositions to a temperature below the setting temperature thereof.

In a more specific embodiment, gelable and gelled photoprocessing solutions are formed and used to process photosensitive media as follows. The gelable composition is heated to a temperature above its gel-critical temperature and applied to the photosensitive medium to be processed. Upon cooling, the composition sets or gels. The gelled composition is allowed to remain upon the medium until photoprocessing is complete, after which it is removed from the medium.

Compositions containing agar and a combination of xanthan gum and locust bean gum have surprisingly been found to exhibit a good balance of properties both in the gelable state and in the gelled state. Besides having the very desirable low-setting temperatures characteristic of pure agar gelled solutions, these compositions are improved in several other important properties. They have excellent elasticity in their gelled state and are not brittle as are compositions gelled solely with agar. In addition, the viscosity of the gelable compositions at elevated extrusion temperatures is significantly increased by the addition of the natural gum gel formers so that these gelable compositions can be conveniently extruded onto a photosensitive medium or other surface. In addition to the aforementioned properties, the compositions gelled as described herein have a number of other good gel properties including excellent break strengths, low tackiness and low syneresis.

DESCRIPTION OF THE PREFERRED EMBODIMENTS

The liquid media of this invention can be a pure liquid such as water. Solutions of solids in liquids and solutions of two or more miscible liquids are also included in the term liquid medium. For example, aqueous solutions of therapeutic agents or photoprocessing agents are gelable as described herein.

Agar is the primary gel former in the compositions of this invention. Agar is a polysaccharide derivative from a seaweed and is generally a polygalactan formed from the sugar units D-galactose and 3,6-anhydro-L-lactose. The structure, properties, preparation, etc. of agar and agar gels is well described in the literature. See for example, Whistler, R. L. and Smart, C. L., *Polysaccharide Chemistry*, Academic Press, Inc. New York (1953) at pp. 207–218. Compositions containing agar generally have gel critical temperatures in the range of about 200°–210°F., but have low setting or gelation temperatures generally around 95°F. As described above, this is a very desirable characteristic for many applications. The presence of cations such as sodium, potassium or ammonium, generally present in photoprocessing solutions, raise the setting temperature of agar gels, but the gelling temperature is still significantly below that of most other gel formers.

The agar is present in an amount of from about 0.5% to about 5% in the compositions described herein. The exact amount will be easily ascertainable by routine experimentation for the particular liquid medium to be gelled. In general, the lowest amount possible that yields good properties upon setting is used. For photoprocessing solutions, it has been found that preferably an amount of about 2% yields the best photoprocessing gels.

A combination of natural gum gel-forming agents including xanthan gum and locust bean gum is used with the agar to form the gelable and gelled compositions. The total amount of this combination of gel formers is low compared to the amount of agar present, and is from about 0.1% to about 0.5% by weight. For photoprocessing compositions, it has been found preferable to use an amount of combination gel former of about 0.3% for the best results.

Xanthan gum is a high molecular weight polysaccharide derived from Xanthomonas Campestris. It contains D-glucose, D-mannose, and D-glucuronic acid as dominant hexose units. For a more detailed discussion of the composition, physical and chemical properties, preparation, etc. of xanthan gum, see the following publications: *Federal Register*, Vol. 34, No. 53, Mar. 1969, Subchapter B, Part 121, Subpart D; *Keltrol*, Technical Bulletin DB No. 18, Kelco Company, Clark, New Jersey.

Locust bean gum is a high molecular weight polysaccharide derived from Ceratonia siliqua. It contains a large proportion of D-galacto-D-mannoglycan in its structure along with smaller amounts of pentoglycan, protein, cellulose and ash. A detailed description of the composition, physical and chemical properties, preparation, etc. of locust bean gum is given in the following literature article: Whistler and BeMiller, *Industrial Gums (Polysaccharides and Their Derivatives)*, Academic Press, New York (1959) at pp. 361–76.

Xanthan gum, locust bean gum, and combinations of these are readily available in commercial quantities under a variety of commercial names. The properties of the commercial products will vary with the particular source and/or the manner of commercial extraction. Some examples of commercial products are as follows:

| Gum | Trademark or Trade Name | Source |
|---|---|---|
| Xanthan Gum | Keltrol | Kelco Co. Clark, N.Y. |
| Locust Bean Gum | Clarified Locust Bean Gum | Marine Colloids Springfield, N.J. |
| 50% Xanthan Gum 50% Locust Bean Gum | Kelgum | Kelco Co. Clark, N.Y. |

Compositions containing mixtures of xanthan gum and locust bean gum normally have gel-critical temperatures in the range of about 150°–170°F., and generally their gelation or setting temperatures are approximately 140°F. As can be seen, their setting temperatures are much higher than those for pure agar gels, and are in fact too high for many gel applications. It is known that gelled compositions using only a combination of xanthan gum and locust bean gum to form the gels require at least 10% xanthan gum and at least 1% locust bean gum in the mixture to form gelled solutions with sufficient break strengths. Therefore, when no other gelling agent is present, these natural gum gel formers are used in amounts of from about 10% to about 99% xanthan gum and from about 1% to about 90% locust bean gum. Likewise, it is even more preferable to use an amount of from about 50% to about 90% xanthan gum and from about 10% to about 50% locust bean gum to obtain the best balance of break strength and elasticities when no other gel formers are used. While these amounts may be preferred when the natural gum gel formers are used with agar, they are not required because the agar provides sufficient break strengths for the gelled solutions.

From the respective amounts of agar and the total natural gum gel formers used, it is apparent that much more agar is used to form the compositions described herein than natural gum formers. While the limits for each have been recited, it should be understood that the most preferable amounts for each for any particular liquid medium can be obtained by routine experimentation to determine the best balance of gel properties in the gelled medium.

Many other embodiments which are within the scope of the appended claims will occur to those skilled in the art.

The following example illustrates the invention even further by way of specific embodiment.

EXAMPLE I

A color-first developer used in reversal color processing is formed from the following ingredients.

| | |
|---|---|
| ethylenediaminetetraacetic acid (EDTA) | 2.0 g |
| sodium sulfite | 50.0 g |
| hydroquinone | 10.0 g |
| graphidone A | 1.0 g |
| 0.5 % Eastman Kodak Anti-Fog No. 73 in 50% Methanol/50% Water | 25.0 milliliters |
| sodium hydroxide | 2.0 g |
| water to | 1.0 liter. |

The pH of the developer solution was 10.0.

To form a gelable color developer solution, the gel formers noted in Table I are added to the developer solution at room temperature. The mixture is then brought to a boil while gentle agitation is used to disperse the gel formers. This gelable composition is air cooled at 120°F., at which point no gelation has occurred, and viscosity measurements are taken at this temperature which is excellent for extrusion. The results are:

Table I

| Gel Formers | Viscosity (centipoises) | Properties |
| --- | --- | --- |
| 2% Agar | 29 | Gelled solution is brittle |
| 2% Agar 0.16% Kelgum | 98 | Gelled soultion has good elasticity and break strength |
| 2% Agar 0.32% Kelgum | 230 | Gelled soultion has good elasticity and break strength. |

As can be seen from Table I, the viscosity of gelable agar compositions is dramatically increased at extrusion temperatures by the use of xanthan gum and locust bean gum combinations. Gelled solutions are formed from the gelable dispersions by cooling them to room temperature. Gelation or setting occurred at 110°F., and the addition of the Kelgum did not noticeably increase this gelation temperature.

What is claimed is:

1. A composition comprising a liquid medium and a combination gelling agent which consists essentially of (a) from about 0.5% to about 5% agar and (b) from about 0.1% to about 0.5% of a mixture of xanthan gum and locust bean gum in a weight ratio of about 10% to about 99% xanthan gum and from about 1% to about 90% locust bean gum.

2. A composition of claim 1 wherein said liquid medium comprises an aqueous solution of a therapeutic agent.

3. A composition of claim 1 in the gelled state.

4. A composition of claim 1 in the gelable state.

* * * * *